United States Patent [19]

Wuchinich

[11] Patent Number: 4,493,694
[45] Date of Patent: Jan. 15, 1985

[54] SURGICAL PRE-ASPIRATOR

[75] Inventor: David G. Wuchinich, New York, N.Y.

[73] Assignee: Cooper LaserSonics, Inc., Santa Clara, Calif.

[21] Appl. No.: 614,691

[22] Filed: May 25, 1984

Related U.S. Application Data

[63] Continuation of Ser. No. 197,869, Oct. 17, 1980, abandoned, which is a continuation of Ser. No. 825,217, Apr. 10, 1979, abandoned.

[51] Int. Cl.³ .............................................. A61B 17/20
[52] U.S. Cl. .................................... 604/22; 128/305; 604/35
[58] Field of Search .................... 32/33; 128/276–278, 128/305, 6, 24 A; 15/341–346, 421; 604/22, 46, 35

[56] References Cited

U.S. PATENT DOCUMENTS

| | | | |
|---|---|---|---|
| 3,589,363 | 6/1971 | Banko et al. | 128/276 |
| 3,693,613 | 9/1972 | Kelman | 128/24 A |
| 3,805,787 | 4/1974 | Banko | 128/276 |
| 3,808,631 | 5/1974 | Shibata et al. | 15/321 |
| 3,902,495 | 9/1975 | Weiss et al. | 128/276 |
| 3,955,573 | 5/1976 | Hanson et al. | 128/276 |
| 3,996,935 | 12/1976 | Banko | 128/276 |
| 4,016,882 | 4/1977 | Broadwin et al. | 128/305 |
| 4,061,146 | 12/1977 | Baehr et al. | 128/305 |
| 4,069,814 | 6/1978 | Clemens | 128/2 F |
| 4,136,700 | 1/1979 | Broadwin et al. | 128/305 |
| 4,180,074 | 12/1979 | Murry et al. | 128/276 |

FOREIGN PATENT DOCUMENTS

| | | | |
|---|---|---|---|
| 1542802 | 9/1968 | France | 15/346 |
| 288842 | 4/1971 | U.S.S.R. | 15/346 |

Primary Examiner—C. Fred Rosenbaum
Assistant Examiner—J. L. Kruter
Attorney, Agent, or Firm—Vorys, Sater, Seymour & Pease

[57] ABSTRACT

In a apparatus for aspirating material into an opening into a passage and along the passage, the apparatus has at least one additional opening or orifice for admitting (pre-aspirating) a fluid into the passage. The fluid facilitates aspirating the material along the passage and thus is preferably adjacent the opening through which the material enters the passage to facilitate the aspiration all along the passage. The apparatus is particularly for surgical use. In surgical uses the material to be aspirated contains blood which tends to coagulate in the passage and block it. The fluid which enters the passage through the orifice then dilutes the blood to reduce coagulation, lubricates the passage for better material flow therealong, and flushes the material along the passage.

4 Claims, 3 Drawing Figures

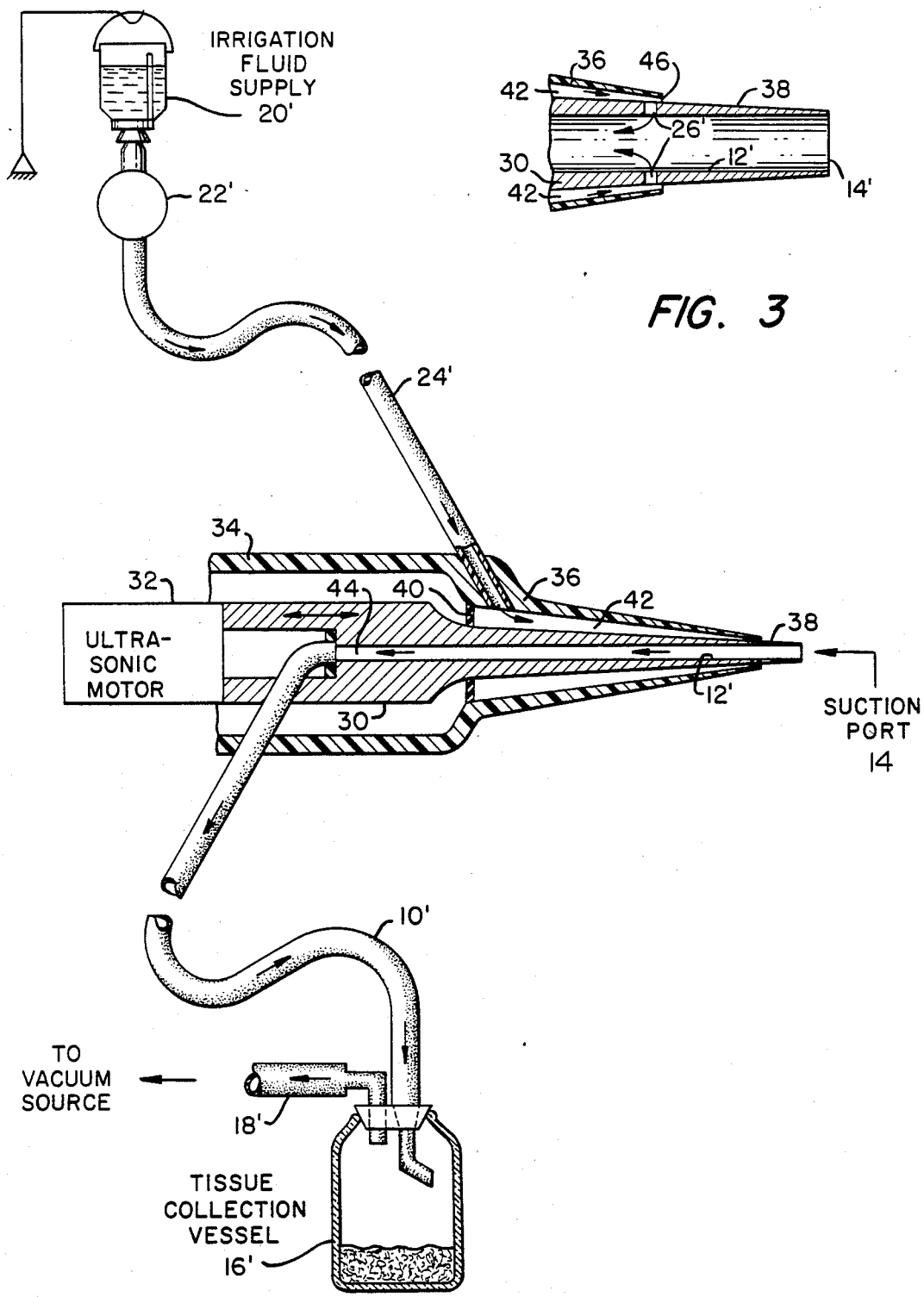

SURGICAL PRE-ASPIRATOR

This application is a continuation of application Ser. No. 197,869 filed Oct. 17, 1980 now abandoned, which is a continuation of Ser. No. 825,217 filed Apr. 10, 1979.

BACKGROUND OF THE INVENTION

Many suction devices are known for moving many different materials into and along a suction passage. One type of such devices which is particularly pertinent to the preferred embodiments of the present invention is for surgery. With these devices, body fluids such as blood, and tissue are sucked away from surgical sites both to remove the material itself, for example a tumor, and to keep the site clear.

The material to be sucked along the passage of these devices in some uses, including surgery, is insufficiently fluid to flow well along the passage, and in surgery, in addition, blood, although normally fluid, naturally coagulates upon removal from the body and contact with foreign matter such as the suction passage to further tend to clog the apparatus. In surgery, therefore, fragments of the body tissue and coagulated blood often clog known suction apparatus. The time and effort for cleaning or replacing the apparatus to maintain its operability is always undesirable and, in surgery, can be critically detrimental.

One way of reducing the clogging of suction devices which is sometimes used in their surgical application is to irrigate the material to be aspirated before it enters the suction device. The combination of the material and the irrigation fluid is then sucked into the device where the irrigation fluid facilitates the movement of the material along the suction passage. Another way of avoiding the clogging problem which is also used in surgical applications to the extent practical, is to increase the cross-section of the passage. In surgical applications, however, the extent to which the cross-section can be enlarged is limited in order to limit the overall cross-section of the apparatus to a practical size. The irrigation of the tissue prior to aspiration also must be limited in surgery to avoid flooding the tissue site and to avoid squirting the irrigation fluid in an attempt at providing the volume of irrigation fluid required to prevent clogging of the suction passage. Even when both the volume of irrigation fluid and cross-section of the suction passage are maximized, the suction passage in surgical suction devices still tends to clog excessively.

Another way of avoiding clogging in some medical devices such as heart-lung machines is to introduce an anti-coagulant such as heparin into the blood. The resulting reduced coagulation of the blood then allows the device to operate without clogging. Such anti-coagulants cannot be introduced into an irrigation fluid for surgical operations, however, because the anti-coagulant will undesirably increase bleeding at the site and impair surgical control of bleeding and may damage the normal function of other tissues.

SUMMARY OF THE INVENTION

It is therefore an object of the invention to provide a method and apparatus which facilitates the movement of material, and particularly blood-containing material, along the suction passage of a suction device or aspirator.

To this end, the invention provides a method of facilitating the movement of material along the passage of a suction device by introducing a fluid into the passage independently of the opening through which the material enters the passage. The fluid dilutes the material, and lubricates and flushes the passage so the material can be more easily sucked along the passage. Although the method may be useful in many known suction devices, it is particularly useful in surgical suction devices because the coagulation of the blood in the surgically removed material and the practical limits on the size of the suction passage often caused the suction passage to clog.

With the method of the invention, however, additional fluid is introduced into the suction passage to dilute the blood and thus reduce its coagulation. The additional fluid also lubricates the passage to reduce the tendency of the blood to coagulate onto the walls of the passage which constricts and eventually blocks it. The additional fluid also helps flush the material along the passage. Inasmuch as the time for cleaning or changing surgical suction devices during surgery can be critical, maintaining the operability of surgical suction devices with the method of the invention is particularly beneficial.

Apparatus for practicing the method comprises fluid supply extending through the suction device to the suction passage for supplying a fluid to the passage independently of an open end of the suction passage, or suction port, through which material enters the passage. Preferably, of course, the fluid supply extends through the suction device adjacent the suction port so as to lubricate and flush substantially all of the passage and dilute the material in the passage as soon as it enters the passage.

A specific preferred embodiment of the invention comprises an ultrasonically vibrated surgical tool having a suction passage extending from the suction port or opening at one end of the tool. The fluid supply comprises a sleeve spaced about the tool with the suction-port end of the tool projecting slightly from the sleeve for use. Irrigation fluid is supplied between the sleeve and the tool. The sleeve is open at the suction port end of the tool, but at least one orifice extends through the tool to the suction passage just upstream of the end of the sleeve. The suction in the suction passage then aspirates at least some of the irrigation fluid through the orifice into the suction passage for the dilution, lubrication, and flushing functions on the material sucked into the suction passage through the suction port. Aspirating at least some of the irrigation fluid into the suction passage prior to its discharge from the open end of the sleeve (and subsequent aspiration through the suction port with the material) explains the "pre-aspirator" title which has been given the invention.

Pre-aspirating irrigation fluid in this way reduces, or in the preferred mode, eliminates the flow of irrigation fluid from the open end of the sleeve. The volume of the irrigation fluid which can dilute, lubricate and flush the suction passage is thus not limited to an amount which will not flood the surgical site or a flow rate from the open end of the sleeve which will not squirt from the device distractingly or disruptively to delicate tissues at the operating site. The invention thus avoids the problems of the prior art.

DESCRIPTION OF THE DRAWINGS

Other advantages and features of the invention are described with reference to preferred embodiments which are intended to illustrate and not to limit the invention and in which:

FIG. 2 is a partly sectional schematic of an ultrasonically vibrated surgical pre-aspirator; and FIG. 3 is an enlarged sectional view of a portion of the pre-aspirator shown in FIG. 2.

DESCRIPTION OF THE PREFERRED EMBODIMENTS

Figure 1:
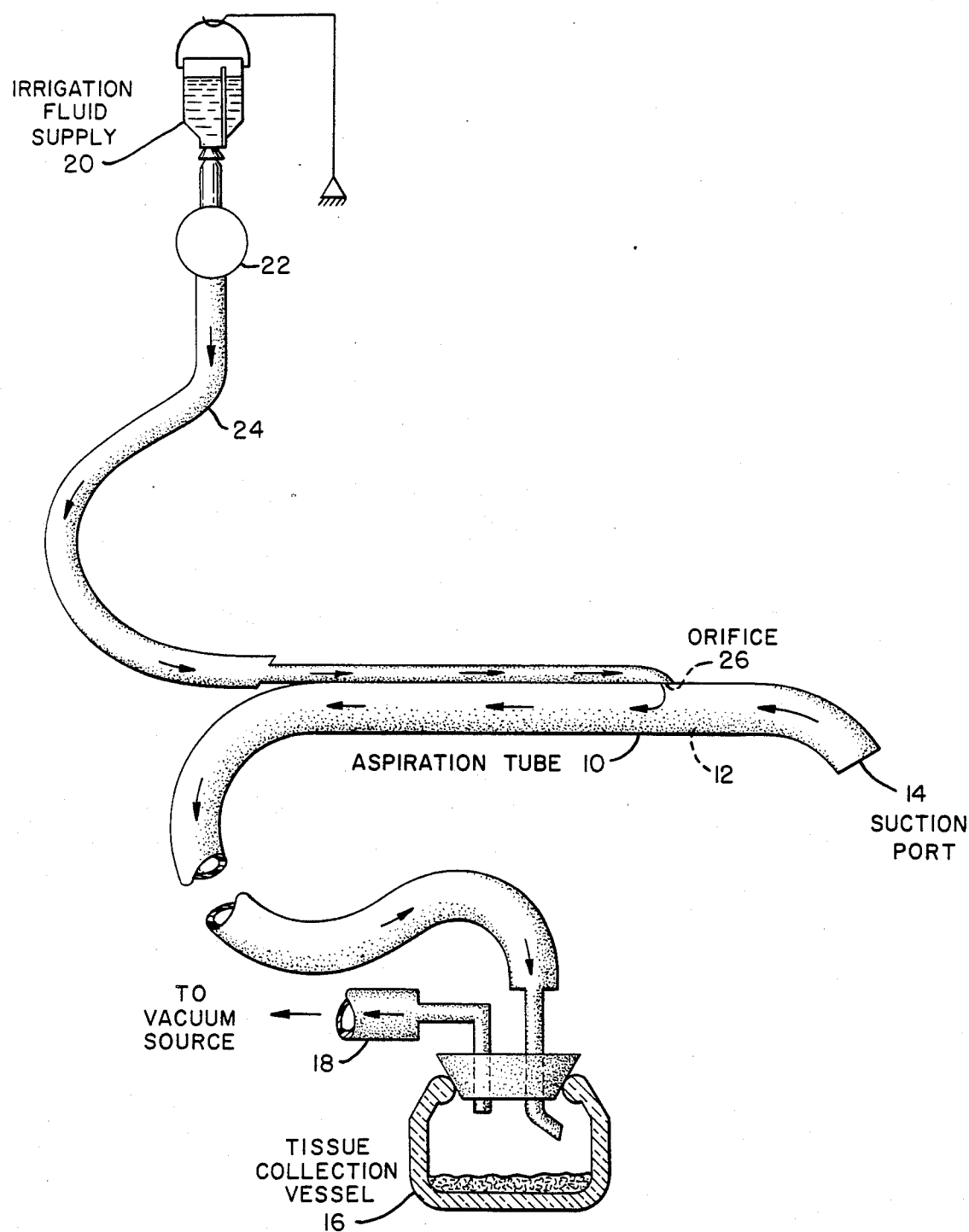
FIG. 1 is a partly sectional schematic of a non-vibrated surgical pre-aspirator.

The preferred embodiment shown in FIG. 1 is a surgical suction device having an aspiration tube 10 with an internal suction passage 12. The suction passage extends from an open end or suction port 14 through which body material such as tissue and blood enters the passage to a tissue collection vessel 16. The tissue collection vessel is sealed and connected to a vacuum source (not shown) by a conduit 18 to apply suction to the suction passage 12 in the aspiration tube 10.

An irrigation fluid supply 20 is connected through a gravity-feed valve or pump 22 and irrigation conduit 24 to an orifice 26. The orifice extends through the aspiration tube to the suction passage 12. Irrigation fluid can thus flow under the control of the valve or pump 22 from the supply 20 into the suction passage 12 to dilute, lubricate and flush the material which enters the aspiration tube through the suction port along the suction passage.

The orifice 26 is positioned adjacent the suction port 14 so that the material entering the passage through the suction port is diluted and flushed and the passage lubricated along substantially its entire length. The orifice is dimensioned relative to the dimensions of the suction port 14 and the suction from the vacuum source such that the desired level of vacuum is obtained at the suction port. In general, therefore, the orifice 26 is smaller than the suction port, but the proper relative dimensioning of the orifice, suction port and vacuum source to obtain the desired suction at the suction port may be varied with the intended use of the device as will be readily understood by those in the art.

FIG. 2 schematically shows another preferred embodiment which is also a surgical suction device, but has an ultrasonically vibrated surgical aspiration tool 30. Ultrasonically vibrated surgical aspiration tools are known; one, for example is described in the assignee's U.S. Pat. No. 3,589,363 issued June 29, 1971 in the names of Banko and Kelman. This patent is incorporated by reference to provide more detailed description of the ultrasonically vibrated surgical aspiration tool 30.

In general, however, the tool 30 is connected to an ultrasonic motor 32 such as an electromagnetically excited magneto-strictive transducer. The motor and tool are mounted in a case or handpiece which is dimensioned to be held in a surgeon's hand. A sleeve 36 is connected to the handpiece and spaced about a portion of the tool. An end 38 of the tool 30 projects slightly from the sleeve 36 and the adjacent end of the sleeve is open about the tool. A seal 40 seals the other end of the sleeve to the tool to form a passage 42 for irrigation fluid between the sleeve and the tool.

Other parts of the preferred embodiment shown in FIG. 2 are substantially similar to the preferred embodiment shown in FIG. 1 and are therefore identified with corresponding reference characters. An irrigation fluid supply 20' is in fluid communication via a pump or valve 22' and conduit 24' with the passage 42 between the sleeve 36 and tool 30; the passage 42 thus forms part of the irrigation fluid conduit 24'. A vacuum source (not shown) is connected through conduit 18', tissue collection vessel 16' and aspiration tube 10' to a passage 44 within the tool 30; the passage 44 thus forms part of the suction passage 12'. The passage 44 has an open end or suction port 14' at the end 38 of the tool which projects beyond the sleeve. The suction passage 12' thus extends from the suction port 14' through the passage 44 and aspiration tube 10' to the vacuum source for providing suction to the passage.

The irrigation fluid passage 42 between the sleeve 36 and tool 30 carries the irrigation fluid about the tool along essentially the length of the tool to cool the tool. The ultrasonic vibrations from the motor 32 vary along the length of the tool, but are at a maximum at the exposed end 38 of the tool. The tool within the sleeve 36 thus has increasing ultrasonic vibrations toward the operative end 38 which, for surgical use of the tool, are in a range which substantially heats the tool. The irrigation fluid in the irrigation passage 42, however, surrounds and cools the tool. In addition to controlling the flow of irrigation fluid for dilution, flushing and lubrication carried along the suction passage 12' as before described, therefore, the control of the irrigation fluid flow with valve or pump 22' thus also provides adequate cooling fluid if the ultrasonic vibration design requires more fluid for cooling than for the dilution, flushing and lubrication of the suction passage. Fluid cooling of ultrasonically vibrated tools is a design consideration understood by those in the art and thus requires no further explanation.

FIG. 3 is an enlarged view of the end 38 of the tool 30 shown in FIG. 2 and corresponding portion of the sleeve 36. As better seen in FIG. 3, the end 46 of the sleeve 36 adjacent the tool end 38 is spaced about the tool 30. The irrigation fluid passage 42 is thus open-ended. Immediately upstream of the end 46 of the sleeve relative to the flow of the irrigation fluid toward the open end of the passage 42 at the sleeve end 46 is a pair of diametrically opposite, identical pre-aspiration orifices 26'. Irrigation fluid from the passage 42 can thus enter the suction passage 12' through the orifices 26' or be discharged from the open end of the irrigation passage 42 at the end 46 of the sleeve. The irrigation fluid entering the suction passage 12' through the orifices 26' dilutes the material entering the suction passage 12' through the suction port 14', flushes the material along the suction passage, and lubricates the walls of the suction passage as before described.

In the preferred mode of operating the ultrasonic pre-aspirator shown in FIGS. 2 and 3, substantially all the irrigation fluid from the passage 42 enters the suction passage 12' through the pre-aspiration orifices 26' by properly dimensioning the fluid supply rate, suction and pre-aspiration orfices 26'. To achieve a fluid flow sufficient to cool an ultrasonic tool vibrating at about 23 kHz with a vibrational amplitude at the tool end 38 of about 100 microns, and to dilute, flush and lubricate body tissue and blood entering the suction port 14' of about 0.1 inch diameter under a suction of about 0.5 atmospheres without discharging irrigating fluid from the open end of the sleeve, the two pre-aspiration orifices are each about 0.015 inch diameter. In an alternative mode of operating the pre-aspirator, however, more irrigation fluid may be supplied to also exit from the open end of the irrigation passage 42. The additional irrigation fluid can then be aspirated from the surgical site through the suction port 14' along with the other body material. Inasmuch as irrigation fluid is also supplied to the suction passage through the pre-aspiration orfices, however, the volume of fluid at the surgical site does not have to be as great as it would be without the pre-aspiration. Flooding the site can thus be avoided.

Inasmuch as the irrigation fluid does not leave the device to contact body tissues in either of the preferred embodiments shown in FIGS. 1 and 2, when the latter is operated in the preferred mode with total pre-aspiration, the irrigation fluid may also include an anti-coagulant to still further reduce the coagulation of blood entering the suction passage through the suction port 14'. The anti-coagulant cannot affect the tissues at the surgical site as in prior structures because it does not leave the device.

The ultrasonic vibration of the tool end 38 fragments tissue contacted by the tool end at a surgical site so that the tissue can be more easily aspirated through suction port 14'. The ultrasonic vibration of the tool or at least the heat thereof, however, also tends to increase the coagulation of blood in the tool-portion 44 of the suction passage 12'. The ultrasonic vibration thus increases the tendency of the aspirated material to block the suction passage. The ultrasonic vibration also tends to atomize irrigation fluid discharged at the tool end 38. The resulting fluid mist obscures vision of the surgical site, but is eliminated in the preferred mode of the pre-aspirator because irrigation fluid does not reach the vibrating, atomizing tool end. The pre-aspiration of irrigation fluid into the suction passage is thus particularly useful with ultrasonically vibrated surgical suction devices.

Other uses and variations of the pre-aspirator, however, are contemplated as within the scope of the invention defined by the following claims in which I claim:

1. An ultrasonic surgical apparatus, comprising:
    a hollow concentric surgical tool having a longitudinal axis;
    means for ultrasonically vibrating said tool for fragmenting body material at a surgical site;
    said tool having an internal suction passage formed along said longitudinal axis for connection to a source of suction;
    said suction passage defining a suction port at an open end of said suction passage for aspirating fragmented body material from the surgical site into said suction passage;
    a sleeve concentrically spaced about and free from contact with said tool, said sleeve extending longitudinal along said tool to substantially the end of said tool adjacent said suction port so as to define a fluid supply passage about said tool for connection to a fluid supply source;
    said sleeve further defining an open annular orifice around said tool at an end face of said sleeve;
    said tool further having at least one pre-aspirating orifice means formed through a wall portion of said tool disposed within said sleeve for admitting at least some fluid into said suction passage; and
    said pre-aspirating orifice means, said suction source, said fluid supply passage and said suction passage each dimensioned to provide means for pre-aspirating substantially all of said fluid through said at least one pre-aspirating orifice so as to prevent substantially all of said fluid flowing from said fluid supply source from reaching said surgical site.

2. The apparatus of claim 1 wherein said at least one pre-aspiration orifice means comprises a first pre-aspiration orifice and a second pre-aspiration orifice each having a diameter of approximately 0.015 inch.

3. The apparatus of claim 2 wherein said suction port has an area at least twice the total area of said first and second orifices.

4. The apparatus of claim 1 wherein each said at least one pre-aspiration orifice has a maximum cross sectional dimension less than one-half the maximum cross sectional dimension of said suction port.

* * * * *